United States Patent [19]

Broadhurst et al.

[11] Patent Number: 4,645,843

[45] Date of Patent: Feb. 24, 1987

[54] PROCESS FOR THE PREPARATION OF N-ARYLHALOPYRROLID-2-ONES

[75] Inventors: Michael D. Broadhurst, Novato; Richard D. Gless, Jr., Oakland, both of Calif.

[73] Assignee: Stauffer Chemical Company, Westport, Conn.

[21] Appl. No.: 704,813

[22] Filed: Feb. 25, 1985

Related U.S. Application Data

[63] Continuation-in-part of Ser. No. 505,135, Jun. 16, 1983, abandoned.

[51] Int. Cl.$^4$ .......................................... C07D 207/26
[52] U.S. Cl. .................................................... 548/543
[58] Field of Search ........................................ 548/543

[56] References Cited

U.S. PATENT DOCUMENTS 4,132,713  1/1979  Broadhurst ........................ 548/543

Primary Examiner—Glennon H. Hollrah
Assistant Examiner—D. B. Springer
Attorney, Agent, or Firm—Edwin H. Baker; Joel G. Ackerman

[57] ABSTRACT

Production of N-arylhalopyrrolidones by intramolecular cyclization of an α-halogen-N-2-alkenylamide is conducted in the presence of a copper-containing catalyst and a primary or secondary aliphatic amine.

20 Claims, No Drawings

PROCESS FOR THE PREPARATION OF N-ARYLHALOPYRROLID-2-ONES

CROSS REFERENCE TO RELATED APPLICATIONS

This application is a continuation-in-part of Application Ser. No. 505,135, filed June 16, 1983, abandoned.

BACKGROUND OF THE INVENTION

Certain N-arylhalopyrrolidones are known to be useful as herbicides of general application. Such compounds and their utility are disclosed in, for instance, U.S. Pat. No. 4,110,105 of Eugene G. Teach.

One process for their production is disclosed in U.S. Pat. No. 4,110,105 and additionally U.S. Pat. No. 4,210,589, which is a division of the former. According to those references, the compounds are prepared by the intramolecular cyclization of an α-halogen-containing N-2-alkenylamide in the presence of a catalytic amount of ferrous iron.

Another U.S. Pat. No. 4,132,713, of Michael D. Broadhurst, discloses an improved method of producing such compounds utilizing catalysts other than ferrous iron. In particular, the catalyst of U.S. Pat. No. 4,132,713 contains one or more of the transition metals vanadium, molybdenum, ruthenium, silver, and copper. The metal-containing compounds may be present in a number of forms, including complexes with common complexing agents such as triphenylphosphine, carbon monoxide, and tertiary amines. Examples of tertiary amines disclosed to be useful in that process are pyridine, 2,2'-dipyridyl, 2,2'-dipyridylamine, and tetramethylethylenediamine. Among the copper-containing compounds specifically disclosed in that patent are cuprous chloride and cupric oxide.

When using copper-containing catalysts with tertiary amine complexing agents, the process may be conducted at a temperature of from about 60° C. to about 200° C., preferably from about 80° C. to about 150° C. Table II of U.S. Pat. No. 4,132,713 shows the results for production of the compound 3-chloro-4-chloromethyl-1-(m-trifluoromethylphenyl)-2-pyrrolidone,

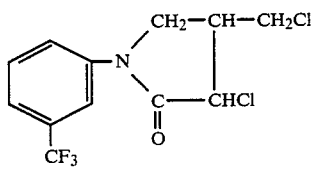

utilizing cupric oxide and cuprous chloride variously complexed with several tertiary amines. The process was conducted at times ranging from 2.5 to 11 hours with yields ranging up to 65% of theoretical. A larger scale preparation of the product is described in Example 14 of the patent. Other examples show production of related compounds by this technique.

SUMMARY OF THE INVENTION

It has now been found that an improvement with respect to the process generally described in U.S. Pat. No. 4,132,713 may be obtained by conducting the reaction in the presence of a catalyst comprising a copper compound together with an amine selected from the group consisting of:

(a) primary amines having the formula $RNH_2$, in which R is a straight- or branched-chain alkyl group having from 1 to 20 carbon atoms, optionally substituted by hydroxy; or (b) secondary amines having the formula $R_1NHR_2$, in which $R_1$ and $R_2$ are independently straight- or branched-chain alkyl groups having from 1 to 20 carbon atoms, optionally substituted by hydroxy, exclusive of branched-chain alkyl groups having the branching at the alpha-carbon atom.

DETAILED DESCRIPTION OF THE INVENTION

The N-2-alkenyl-α-haloamide which is used as a starting material in the process of the present invention may be prepared by any conventional technique known in the art. Several techniques are provided in U.S. Pat. No. 4,132,713.

The N-arylhalopyrrolidones produced according to the present invention have the general formula

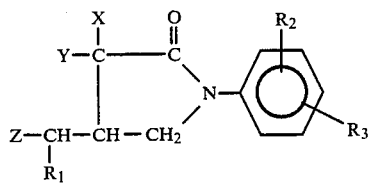

X is selected from the group consisting of hydrogen, chlorine, bromine and fluorine;

Y is selected from the group consisting of hydrogen, chlorine, bromine and fluorine;

Z is selected from the group consisting of chlorine and bromine;

$R_1$ is selected from the group consisting of hydrogen and $C_1$-$C_4$ alkyl;

$R_2$ is selected from the group consisting of hydrogen, $C_1$-$C_4$ alkyl, acetyl, chlorine, bromine, fluorine, iodine, trifluoromethyl, nitro, cyano, $C_1$-$C_4$ alkoxy, $C_1$-$C_4$ alkylthio, $C_1$-$C_4$ alkylsulfinyl, $C_1$-$C_4$ alkylsulfonyl, trifluoromethylthio, trifluoromethylsulfinyl, trifluoromethylsulfonyl, pentafluoropropionamido, and 3-methylureido; and $R_3$ is selected from the group consisting of hydrogen, $C_1$-$C_4$ alkyl, chlorine, and trifluoromethyl.

A class of preferred products are those in which $R_3$ is trifluoromethyl and $R_2$ is hydrogen or fluoro. One preferred product is 3-chloro-4-chloromethyl-1-(m-trifluoromethylphenyl)-2-pyrrolidone (X=chloro, Y=hydrogen, Z=chloro, $R_1$=hydrogen, $R_2$=hydrogen, $R_3$=3-trifluoromethyl).

The cyclization of the N-2-alkenyl-α-haloamide is conducted in the presence of a catalyst comprising a copper compound. The copper compound is preferably cuprous chloride, cupric chloride or cupric oxide, with cuprous chloride being most preferred.

The catalyst can either be present as an undissolved solid in the reaction mixture, or as a solute in solution with the starting amide or solvent, when a solvent is used. In general, the catalyst is preferably dissolved. The reaction will proceed without agitation, whether the catalyst is undissolved or in solution. However, when agitation is used, the progress of the reaction will be significantly enhanced. Agitation may be achieved by any conventional means, for instance stirring, inert gas purging, the use of baffles in the reaction vessel, or conducting the reaction at reflux.

The quantity of copper-containing catalyst which will constitute a catalytic amount will be that quantity which serves to increase the rate of reaction. Larger quantities will provide a greater increase. The quantity used in any particular application will be determined in large part by the individual needs of the manufacturing facility. Aside from considerations such as cost, the desired reaction time and system capacity, the catalyst quantity is not a critical feature in the invention and may vary over a wide range. Most conveniently, an amount of catalyst is used which comprises from about 0.1 to about 20.0 mole percent, based on the initial quantity of the N-2-alkenylamide.

Preferred quantities of catalyst are: for cuprous or cupric chloride—from about 1 to about 10 mole percent; for cupric oxide—from about 1 to about 5 mole percent.

The amines which have been found useful in the improved process of this invention are certain primary and secondary aliphatic amines.

The primary amines are of the type $RNH_2$, in which R is a straight- or branched-chain alkyl group having from 1 to 20 carbon atoms, optionally substituted by hydroxyl. Such amines would include, for instance, ethylamine, propylamines, various butylamines, and amines containing higher alkyl groups. One example of a hydroxy-substituted alkyl amine is 6-hydroxyhexylamine.

The secondary amines are of the $R_1NHR_2$, in which $R_1$ and $R_2$ are alkyl groups having from 1 to 20 carbon atoms, preferably from 1 to 12 carbon atoms. These alkyl groups may be straight- or branched-chain groups, optionally substituted by hydroxy, with the proviso that if branched-chain, the branching is other than at the alpha-carbon atom. Secondary amines containing alpha-branched alkyl groups, such as isopropyl, sec-butyl, and the like, do not provide advantageous results in this process. The alkyl groups $R_1$ and $R_2$ may be the same or different; preferably they are the same. A preferred class of secondary amines are those in which $R_1$ and $R_2$ are identical straight-chain alkyl groups having from 1 to 12 carbon atoms. Preferred members of this class are di(n-butyl) and di-(n-propyl)amines.

If desired, a variety of solvents may be used in the reaction. Such solvents may include aliphatic compounds such as heptane or octane, alcohols such as tertiary butyl alcohol, and aromatic compounds such as toluene or xylene. Preferred solvents are toluene and tertiary butyl alcohol. Other inert solvents such as those mentioned in U.S. Pat. No. 4,132,713 may be employed if desired.

The amount of amine used may vary widely according to the costs and effect desired. In general, the amine is utilized in an amount of from about 5 to about 60 mole percent, based on the starting N-2-alkenyl-α-haloamide, and preferably from about 10 to about 40 mole percent.

The temperature at which the process is conducted is generally from about 50° C. to about 150° C. Preferred operating ranges will vary, depending on the nature of the copper-containing catalyst, the amine, the solvent (if any), and the concentration of the α-haloamide in the substrate. Generally, cuprous chloride and lower molecular weight amines containing up to eight carbon atoms per alkyl group perform best at temperatures of from about 60° to about 90° C.

As the reaction occurs in the liquid phase, the operating pressure is not a significant parameter, and may range widely, depending on convenience, economy and materials of construction. It is most convenient to conduct the reaction at or near ambient pressure.

If the reaction is conducted in the presence of a solvent, under reflux or at or near atmospheric pressure, the temperature may be the normal reflux temperature of the solvent, or may be lower. Temperatures of about 85° C. have been found advantageous for solvents such as toluene nd tertiary butyl alcohol.

The concentration of α-haloamide in the solvent may vary. However, as the concentration is increased from about 20 weight % to about 60 weight %, selectivity and yield of the reaction generally decrease, with the production of less desired products and greater amounts of "tars". This is particularly true for higher molecular weight amines and cupric oxide catalysts. For good results, therefore, the concentration of the amide in the solvent should be at a maximum of about 65 weight %, most preferably about 40 weight %.

The order of addition of materials is not a significant parameter. However, it is preferable to pre-mix the copper catalyst and amine, and then add the α-haloamide, as this can produce a small improvement in yield.

A preferred set of parameters for carrying out this process are:
copper catalyst: 3–8 mole %
amine: 20–40 mole %
solvent: toluene
temperature: 75°–95° C.
amide concentration in solvent: 15–30%

The pyrrolidone produced by the reaction can be recovered from the reaction mixture by any conventional technique, such as solvent extraction, crystallization, sublimation, or distillation.

As compared with the copper-tertiary amine complexes described in U.S. Pat. No. 4,132,713, the use of a copper catalyst with a primary or secondary aliphatic amine of the type described herein results in the production of a greater yield of the desired compound, with a corresponding decrease in the production of non-volatile by-products ("tars"), and generally a decrease in the necessary reaction time.

The following examples illustrate the conduct of the process, with respect to the production of the compound 3-chloro-4-chloromethyl-1-(m-trifluoromethylphenyl)-2-pyrrolidone.

EXAMPLE 1

In a flask were mixed 200 grams (g.) (0.567 mole) N-allyl-3'-trifluoromethyl-2,2-dichloroacetanilide, 2.79 g. (0.028 mole) cuprous chloride, 28.5 milliliters (ml.) (0.169 mole) di-(n-butyl)amine, and 891 ml. toluene. The mixture was heated to a temperature of 85°–90° C. and stirred for 2 hours and 25 minutes. At the end of this time, a sample of the reaction mixture was analyzed by gas chromatography and showed 95.0 area percent of the desired product.

The reaction mixture was washed three times with 125 ml of 3.0M hydrochloric acid. Next, the mixture was phase separated and stripped with an aspirator for one hour at 40° C. and under high vacuum for one hour at 55° C., giving a crude yield of 192.82 g. Analysis by gas chromatography showed a purity of 86.8%, corresponding to a corrected yield of 94.5% of the desired product. Distillation of a sample showed that the product contained 5.8 weight % non-volatile tars. The structure of the desired product was confirmed by mass spectroscopy.

COMPARISON EXAMPLE 1

This example illustrates the conduct of the process utilizing a cupric oxide/pyridine catalyst as in U.S. Pat. No. 4,132,713.

In a flask there were mixed 200 g. (0.586 mole) N-allyl-3'-trifluoromethyl-2,2-dichloroacetanilide, 8.25 g. (0.058 mole) cupric oxide, 18.7 ml. (0.023 mole) pyridine, and 135 ml. toluene. The mixture was heated to a reflux at 115° C. and stirred for a total of one hour, 20 minutes. The mixture was filtered, then washed three times with 100 ml of 3.0M hydrochloric acid. Next, the mixture was phase separated and stripped first with an aspirator, then under high vacuum for one hour at 55° C. to give a crude yield of 186.80 g. By gas chromatography, the reaction product was shown to be 80.0% pure, which corresponds to a corrected yield of 81.7% of the desired product. The product contained 14.8 weight % tars, as determined by distillation. The structure of the desired product was confirmed by mass spectroscopy.

EXAMPLE 2

In a flask were mixed 0.157 g. (0.00158 mole) cuprous chloride, 1.6 ml. (0.0091 mole) di-(n-butyl)amine, and 40 ml. toluene. The mixture was stirred to dissolve the cuprous chloride. Then, 11.22 g. (0.0334 mole) of the acetanilide utilized in Example 1 was added, together with an additional 10 ml. toluene. The resulting mixture was heated to 85°-95° C. and stirred for 1.5 hours.

At the end of this time the mixture was cooled, washed with 3M hydrochloric acid and stripped under vacuum, to produce 11.81 g. of an orange oil, which was analyzed by mass spectroscopy and shown to be the desired pyrrolidone product. Gas chromatographic analysis of the product showed it to be 85.4% pure, which corresponds to a corrected yield of 96.7%. Distillation of a portion of the product showed it to contain 3.1% by weight of "tars".

EXAMPLES 3–14

The following examples represent conduct of the process according to this invention with other primary and secondary alkyl amines. These examples were all carried out by the following procedure.

The same acetanilide as in Examples 1 and 2 was mixed with 5 mole percent cuprous chloride and 28 mole percent of the indicated amine, utilizing tertiary butyl alcohol or toluene as the solvent. Reactions were carried out at approximately 85° C., or about 115° C. when indicated, for the indicated time. Concentration of the acetanilide in the solvent was about 20-21 weight % except where indicated.

The reaction mixture was washed with dilute aqueous hydrochloric acid, the solvent removed and the products distilled. The reaction products were analyzed for percent by weight of the desired pyrrolidone, and of non-volatile side products ("tars"). Results of these experiments are shown in the following Table I.

TABLE I

| Example No. | Amine | Time, min. | Pyrrolidone Yield, %* | tar, wt. % |
|---|---|---|---|---|
| 3 | HO(CH$_2$)$_6$NH$_2$ | 60 | 86.7 | 5.4 |
| 4 | i-C$_4$H$_9$NH$_2$ | 120 | 84.5 | 4.4 |
| 5 | sec.-C$_4$H$_9$NH$_2$ | 120 | 88.2 | 4.4 |

TABLE I-continued

| Example No. | Amine | Time, min. | Pyrrolidone Yield, %* | tar, wt. % |
|---|---|---|---|---|
| 6 | (n-C$_3$H$_7$)$_2$NH** | 120 | 90.3 | 5.7 |
| 7 | (n-C$_3$H$_7$)$_2$NH | 85 | 88.6 | 5.2 |
| 8 | (n-C$_4$H$_9$)$_2$NH** | 170 | 91.3 | 6.2 |
| 9 | (n-C$_4$H$_9$)$_2$NH | 60 | 90.6 | 7.6 |
| 10 | (n-C$_{12}$H$_{25}$)$_2$NH | 100 | 88.7 | 7.6 |
| 11 | (n-C$_{12}$H$_{26}$)$_2$NH*** | 30 | 82.1 | 20.6 |
| 12 | (n-C$_{18}$H$_{27}$)$_2$NH | 75 | 89.3 | 24.2 |
| 13 | (C$_2$H$_5$)$_2$NH | 60 | 84.8 | 4.2 |
| 14 | (i-C$_4$H$_9$)$_2$NH | 150 | 93.3 | 3.6 |

*Corrected for unreacted starting material, if any.
**Toluene used as solvent.
***Toluene used as solvent, temperature = 115° C., acetanilide concentration in solvent 61 weight %.

COMPARISON EXAMPLE 2

The process was carried out as described for Examples 3-12 above with tertiary butyl alcohol, and cuprous chloride, at 85° C., but using pyridine as the amine rather than a primary or secondary amine. Results obtained were as follows:

Pyrrolidone yield (corrected for unreacted starting material): 89.0 wt. %
Tars (corrected for unreacted starting material): 6.5 wt. %
Time for Reaction: 320 min.

Thus, when using pyridine, a tertiary amine described in U.S. Pat. No. 4,132,713, with the same amount of cuprous chloride as in Examples 3-14, completion of the reaction to achieve comparable yields required nearly 2.5 times as long as with the primary and secondary amines.

EXAMPLES 15–18

These examples demonstrate the conduct of the process utilizing cupric chloride in combination with lower and higher molecular weight amines. The process was carried out as above; experiments utilizing tertiary butyl alcohol as the solvent were conducted at 85° C., with an acetanilide concentration of 21 weight %, those utilizing toluene as the solvent were conducted at 115° C., with an acetanilide concentration of 61 weight %. Results are summarized in the following Table II.

TABLE II

| Example No. | Amine | Solvent | Time, min. | Pyrrolidone Yield, %* | tar, wt. % |
|---|---|---|---|---|---|
| 15 | (n-C$_4$H$_9$)$_2$NH | t-butanol | 135 | 92.1 | 5.9 |
| 16 | (n-C$_{12}$H$_{22}$)$_2$NH | t-butanol | 110 | 84.4 | 15.7 |
| 17 | (n-C$_4$H$_9$)$_2$NH | toluene | 60 | 85.5 | 12.1 |
| 18 | (n-C$_{12}$H$_{22}$)$_2$NH | toluene | 60 | 74.4 | 21.0 |

*Corrected for unreacted starting materials, if any.

The foregoing examples are merely intended to illustrate the conduct of the present process, and are not intended to limit the scope of the invention, except as defined in the following claims.

What is claimed is:

1. In a process for the preparation of N-arylhalopyrrolidones having the formula

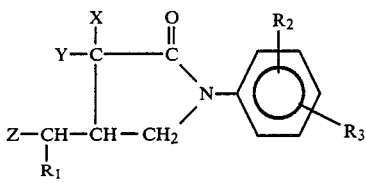

in which
X is selected from the group consisting of hydrogen, chlorine, bromine and fluorine;
Y is selected from the group consisting of hydrogen, chlorine, bromine and fluorine;
Z is selected from the group consisting of chlorine and bromine,
$R_1$ is selected from the group consisting of hydrogen and $C_1$–$C_4$ alkyl;
$R_2$ is selected from the group consisting of hydrogen, $C_1$–$C_4$ alkyl, acetyl, chlorine, bromine, fluorine, iodine, trifluoromethyl, nitro, cyano, $C_1$–$C_4$ alkoxy, $C_1$–$C_4$ alkylthio, $C_1$–$C_4$ alkylsulfinyl, $C_1$–$C_4$ alkylsulfonyl, trifluoromethylthio, trifluoromethylsulfinyl, trifluoromethylsulfonyl, pentafluoropropionamido and 3-methylureido; and
$R_3$ is selected from the group consisting of hydrogen, $C_1$–$C_4$ alkyl, chlorine, and trifluoromethyl, by internal cyclization of the corresponding N-2-alkenyl-α-haloamide in the presence of a copper-containing catalyst, the improvement comprising conducting the internal cyclization at a temperature of from about 50° to about 150° C. in the presence of an amine selected from the group consisting of:

(a) primary amines having the formula $RNH_2$, in which R is a straight- or branched-chain alkyl group having from 1 to 20 carbon atoms, optionally substituted by one hydroxy on a terminal carbon atom; and (b) secondary amines having the formula $R_1NHR_2$, in which $R_1$ and $R_2$ are independently straight- or branched-chain alkyl groups having from 1 to 20 carbon atoms, optionally substituted by one hydroxy per alkyl group on a terminal carbon atom, exclusive of branched-chain alkyl groups having the branching at the alpha-carbon atom.

2. A process according to claim 1 in which the copper containing-catalyst is cuprous chloride.

3. A process according to claim 2 in which the temperature is from about 60° C. to about 110° C.

4. A process according to claim 2 in which the temperature is from about 70° C. to about 90° C.

5. A process according to claim 1 in which the copper containing-catalyst is cupric oxide.

6. A process according to claim 1 in which the copper containing-catalyst is cupric chloride.

7. A process according to claim 1 in which the amine is a primary amine.

8. A process according to claim 7 in which the amine is n-butyl amine.

9. A process according to claim 7 in which the amine is isobutyl amine.

10. A process according to claim 7 in which the amine is secondary butyl amine.

11. A process according to claim 7 in which the amine is 6hydroxy-n-hexyl amine.

12. A process according to claim 1 in which the amine is a secondary amine.

13. A process according to claim 12 in which the amine is di(n-propyl)amine.

14. A process according to claim 12 in which the amine is di(n-butyl)amine.

15. A process according to claim 1 in which the copper containing-catalyst is utilized in an amount of from about 2.5 to about 5 mole percent based on the α-haloamide.

16. A process according to claim 1 in which the time required to complete the reaction is from about 30 to about 180 minutes.

17. A process according to claim 1 in which $R_3$ is trifluoromethyl.

18. A process according to claim 17 in which $R_2$ is fluoro.

19. A process according to claim 17 in which X is chloro, Y is hydrogen, Z is chloro, $R_1$ is hydrogen and $R_2$ is hydrogen.

20. A process according to claim 1 in which the amine is a secondary amine and the copper-containing catalyst is cuprous chloride.

* * * * *